US00PP33600P2

(12) United States Plant Patent
Draheim et al.

(10) Patent No.: US PP33,600 P2
(45) Date of Patent: Nov. 2, 2021

(54) ***ASARUM* PLANT NAMED 'NONERTSUL'**

(50) Latin Name: *Asarum europaeum*
Varietal Denomination: Nonertsul

(71) Applicant: Hortech, Inc., Nunica, MI (US)

(72) Inventors: Gerald Draheim, Grand Haven, MI (US); Sandra Draheim, Grand Haven, MI (US)

(73) Assignee: HORTECH, INC., Spring Lake, MI (US)

( * ) Notice: Subject to any disclaimer, the term of this patent is extended or adjusted under 35 U.S.C. 154(b) by 0 days.

(21) Appl. No.: 17/180,368

(22) Filed: Feb. 19, 2021

(51) Int. Cl.
*A01H 5/00* (2018.01)
*A01H 6/00* (2018.01)

(52) U.S. Cl.
USPC ..... Plt./263.1

(58) Field of Classification Search
USPC ..... Plt./263.1
CPC ..... A01H 5/02; A01H 5/00; A01H 6/00
See application file for complete search history.

*Primary Examiner* — June Hwu
(74) *Attorney, Agent, or Firm* — Penny J. Aguirre

(57) ABSTRACT

A new cultivar of *Asarum europaeum* plant named 'Nonertsul' that is characterized by its long petioles, its large leaves that are kidney-shaped and very dark green in color with a very shiny surface, its vigorous growth habit, and its flowers that are large in size and held beneath the foliage.

2 Drawing Sheets

Botanical classification: *Asarum europaeum.*
Cultivar designation: 'Nonertsul'.

BACKGROUND OF THE INVENTION

The present invention relates to a new and distinct cultivar of *Asarum europaeum*, is hereinafter referred to by the cultivar name 'Nonertsul'. 'Nonertsul' represents a new herbaceous perennial, European ginger, grown for use as a landscape plant.

'Nonertsul' was discovered by the Inventors as a chance seedling in their home garden in Grand Haven, Mich. in June of 2010 amongst plants of unnamed and unpatented plants of *Asarum europaeum* that were growing in the garden. The exact parents are therefore unknown.

Asexual propagation of the new cultivar was first accomplished by the Inventors by division in June of 2010 in Grand Haven, Mich. Propagation by division has determined the characteristics to be stable and reproduced true to type in successive generations.

SUMMARY OF THE INVENTION

The following traits have been repeatedly observed and represent the characteristics of the new cultivar. These attributes in combination distinguish 'Nonertsul' as a new and unique cultivar of *Asarum.*

1. 'Nonertsul' exhibits long petioles.
2. 'Nonertsul' exhibits large leaves that are kidney-shaped and very dark green in color with a very shiny surface.
3. 'Nonertsul' exhibits a vigorous growth habit.
4. 'Nonertsul' exhibits flowers that are large in size and held beneath the foliage.
5. Petals none.

'Nonertsul' can be compared to typical plants of the species *Asarum europaeum*, including those growing in the area of discovery. Typical plants of *Asarum europaeum* differ from 'Nonertsul' in having smaller flowers with smaller flower buds that are less covered by cataphylls, and that are more maroon in color, smaller and more numerous leaves that are lighter green in color, a more compact plant habit, shorter plant height, petioles that are shorter, less strong, and held at in a more whorled angle, and a less vigorous growth habit.

BRIEF DESCRIPTION OF THE DRAWINGS

The accompanying colored photographs illustrate the overall appearance and distinct characteristics of the new *Asarum*. The photographs were taken of a plant 18 months in age in age as grown outdoors in a garden in Grand Haven, Mich.

The photograph in FIG. 1 provides a top view of 'Nonertsul'.

Figure 1:
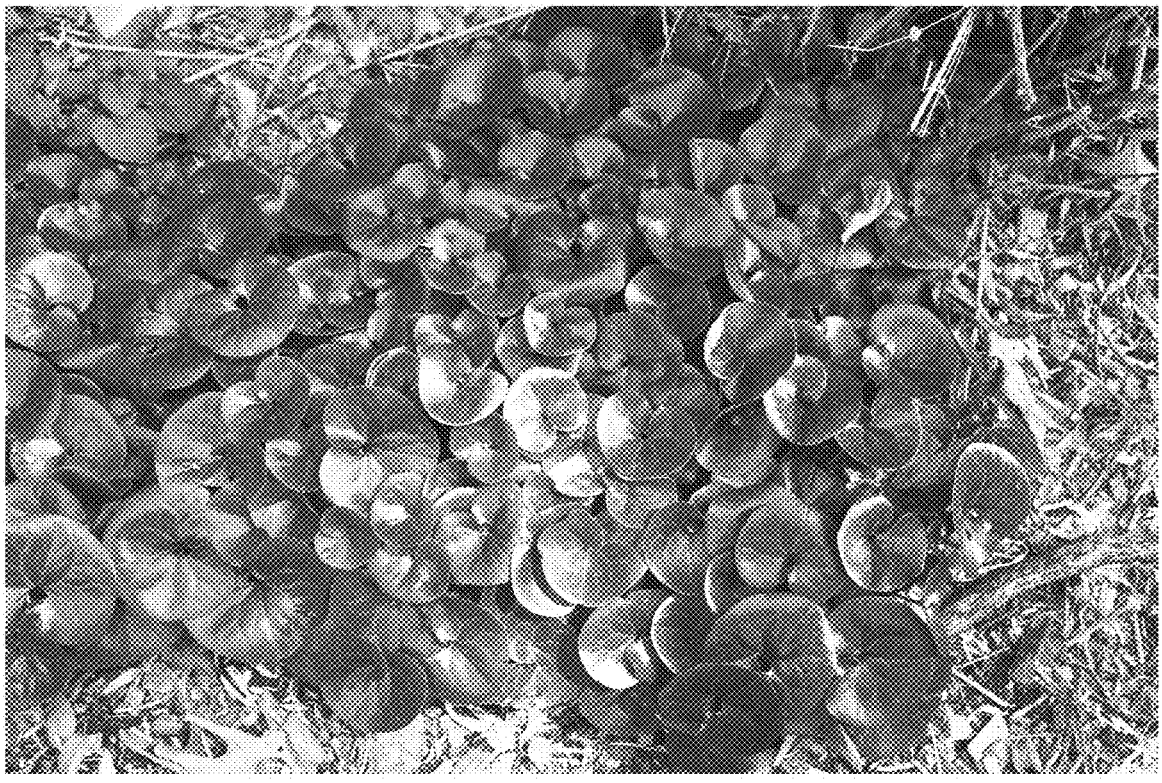
Figure 2:
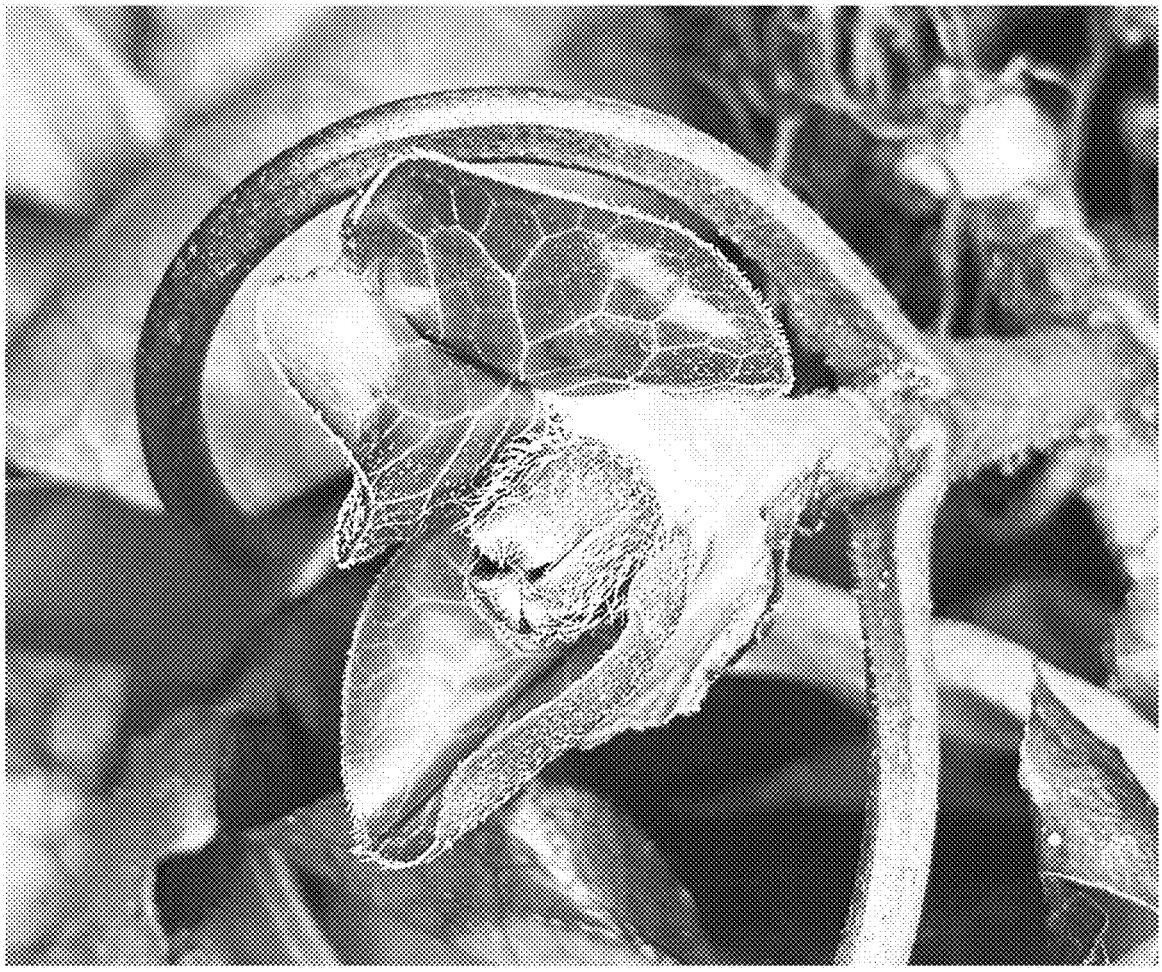

The photograph in FIG. 2 provides a close-up view of a flower of 'Nonertsul'.

The colors in the photographs may differ slightly from the color values cited in the detailed botanical description, which accurately describe the colors of the new *Asarum.*

DETAILED BOTANICAL DESCRIPTION OF THE PLANT

The following is a detailed description of 18-month-old plants of the new cultivar as grown in a landscape bed Grand Haven, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Spring in Michigan.
*Plant type.*—Herbaceous perennial.
*Plant habit.*—Clump-forming, mounded habit.
*Height and spread.*—Average of 13 cm in height and 27 cm in width.

*Cold hardiness*.—At least in U.S.D.A. Zone 4.

*Diseases and pests*.—No susceptibility and resistance to diseases or pests has been observed, however black spot (causative agent could be *Pseudomonas* sp. or a number of fungus species) has not been observed on the new cultivar although observed on other *Asarum europaeum* growing in the area.

*Root description*.—Fleshy, fibrous and dense, 161D in color.

*Branching habit*.—No branches, leaves grow from the base, flower blooms at the base.

*Propagation*.—Division.

*Growth rate*.—Vigorous.

Foliage description:

*Leaf shape*.—Reniform.

*Leaf division*.—Single.

*Leaf base*.—Cordate, lobes at the base slightly overlapping and curled.

*Leaf apex*.—Obtuse.

*Leaf venation*.—Palmate, color of upper surface; 145A, color lower surface; 139A.

*Leaf margins*.—Entire and slightly undulate.

*Leaf attachment*.—Petiolate.

*Leaf arrangement*.—Opposite.

*Leaf surface*.—Upper surface is very glossy, leathery and slightly rugose, lower surface is slightly glossy and rugose, both surfaces are rough to the touch due to being moderately pubescent with short hairs, more densely on the veins; average of 0.3 mm in length and NN155D in color and slightly translucent.

*Leaf color*.—Young and mature upper surface; darker than NN137A and slightly tinged with 203A, young and mature lower surface; 148A.

*Leaf size*.—Average of 8 cm in length and 10 cm in width, lobe depth 3 cm, opening width 1 cm.

*Leaf quantity*.—Average of 21.

*Petioles*.—Average of 11 cm in length and 3 mm in width, color 144A, slightly flushed at the base with 184A, densely covered with short stiff pubescent hairs, 0.3 mm in length, NN155C in color.

Flower description:

*Inflorescence type*.—Solitary, terminal and nodding, held below the foliage.

*Flower fragrance*.—Slightly fresh and pungent, ginger-like.

*Flower quantity*.—3 per stem.

*Flower lastingness*.—Average of two weeks.

*Flower buds*.—Ovate, covered in cataphyll, flattened in shape, spear-shaped, pointed apex, cordate base, average of 3.5 cm in depth and 1.5 cm in width, color 144A, slightly flushed at the base with 184A, densely covered with short stiff pubescent hairs, 0.3 mm in length, NN155C in color.

*Flower shape*.—Bell shaped.

*Flower aspect*.—Held upright to horizontal.

*Flower size*.—Up to 1.5 cm in depth, 1.2 cm in width.

*Sepals*.—3, in a star shape, broadly obovate in shape, lower 40% fused at base, margin is entire, about 1 cm in length and 3 mm in width, narrowly acuminate and reflexed tips, upper and lower surfaces are glossy and moderately velvety, outer surface heavily covered with long, soft woolly hairs NN155A in color, 3 mm in length, color: when opening upper side; N186A, when opening lower side; 187A, when fully opened upper side; 187A, when fully opened lower side; N186A.

*Cataphyll*.—6 in three layers, upper layers; 2, held directly on each side of the flower up to 3 cm in length and width, opposite, reniform in shape, margins are entire, apex is rounded, cordate base, both surfaces are very glossy, stem and base of cataphyll heavily covered with long, soft woolly hairs NN155A in color, 3 mm in length, color of upper (inner) surface 139A, color of lower (outer) surface N187A, middle layers; 2, held below the upper layers up to 1.5 cm in length, 1 cm in width, opposite, reniform in shape, margins are entire, apex is bluntly acute, cordate base, both surfaces are very glossy, base and tips of cataphyll heavily covered with long, soft woolly hairs NN155A in color, 1.5 mm in length, color of both surfaces a blend of 144A and N186A and 157A, lower layers; 2 held at the very base 1 cm in length, 5 mm in width, opposite, ovate in shape, margins are entire, apex is acute, base is fused, both surfaces are very glossy and becoming dry as the mature, base and tips of cataphyll heavily covered with soft woolly hairs NN155A in color, 0.5 mm in length, color of both surfaces a blend of 144A and N186A.

*Receptacle*.—5 mm in diameter.

Reproductive organs:

*Gynoecium*.—Pistils; 6, 2 mm in length, stigma; club-shaped and N187A in color, style; is 1.8 mm in length and N155C in color, ovary; 4 mm in length and diameter, rounded, ovules; many tiny round ovules inside ovary, glossy surface, 0.5 mm in diameter, NN155A in color.

*Androecium*.—8 stamens, anther; attached at the base, oval and bifid in shape, 0.5 mm in diameter, 182B and 183B in color, filament; 3 mm in length, 183A in color, base fused to anthers, pollen; moderate in quantity, NN155A in color.

*Seed*.—No fruits or seed detected to date.

It is claimed:

1. A new and distinct cultivar of *Asarum* plant named 'Nonertsul' as herein illustrated and described.

* * * * *